United States Patent [19]

Mittleman et al.

[11] Patent Number: 5,311,126
[45] Date of Patent: May 10, 1994

[54] MAGNETIC FIELD STRENGTH THRESHOLD INDICATOR FOR USE IN A MAGNETIC PARTICLE INSPECTION DEVICE

[75] Inventors: John Mittleman, Panama City, Fla.; Robert DeNale, Arnold; Lawrence M. Brown, Annapolis, both of Md.

[73] Assignee: The United States of America as represented by the Secretary of the Navy, Washington, D.C.

[21] Appl. No.: 943,622

[22] Filed: Sep. 11, 1992

[51] Int. Cl.$^5$ ............... G01R 35/00; G01R 33/02; G01N 27/84

[52] U.S. Cl. ............................... 324/202; 324/216; 324/228; 324/258

[58] Field of Search ............... 324/202, 216, 217, 228, 324/229, 230, 239, 240, 103 P, 133, 244, 258, 260; 361/160

[56] References Cited

U.S. PATENT DOCUMENTS

| | | | |
|---|---|---|---|
| 2,311,715 | 2/1943 | Thorne | 324/217 |
| 3,309,690 | 3/1967 | Moffitt | 324/133 X |
| 3,857,081 | 12/1974 | Gebelein, Jr. | 361/160 X |
| 4,634,969 | 1/1987 | Edlin et al. | 324/258 X |
| 4,635,142 | 1/1987 | Haugland | 324/103 P X |
| 4,956,600 | 9/1990 | Severinsky | 324/103 P X |

FOREIGN PATENT DOCUMENTS 460991 5/1935 United Kingdom ............... 324/230

OTHER PUBLICATIONS

Hoel, J. E., Magnetic Reluctance, Film Thickness Gauge IBM Tech. Discl. Bull., vol. 13, No. 10, Mar. 1971, pp. 3048-3049.

Primary Examiner—Gerard R. Strecker
Attorney, Agent, or Firm—Charles D. Miller

[57] ABSTRACT

Field strength of an electromagnet is monitored at a threshold with a coupling coil positioned to monitor magnetic flux in a leg of an electromagnet. In the context of magnetic particle inspection for surface flaws (e.g. cracks) in ferromagnetic materials, sensing magnetic flux in a portion of a magnetic circuit including the material being inspected provides a continuous direct indication of whether or not the magnetic field strength produced is sufficient for reliable inspection to be performed. Since the magnetic flux in the electromagnet will be reduced with increases in reluctance of the magnetic circuit, the continuous monitoring of magnetic field strength also effectively monitors correct inspection technique by the magnetic particle inspection methodology.

1 Claim, 2 Drawing Sheets

MAGNETIC FIELD STRENGTH THRESHOLD INDICATOR FOR USE IN A MAGNETIC PARTICLE INSPECTION DEVICE

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

1. Field of the Invention

The present invention generally relates to material inspection and, more particularly, to apparatus for inspection for surface cracks in ferromagnetic materials.

2. Description of the Prior Art

Ferromagnetic materials such as iron and steel are used in the construction of many structures. When employed in load bearing members of such structures, such materials are often subjected to bending moments. These bending moments are carried within the members generally as either tension or compression which will usually vary from point to point within the volume of the structural member and be maximized at the surface of the structural member.

During the fabrication of iron and steel structural shapes and plates, the iron or steel is typically brought to final dimensions by repetitively passing it through spaced, shaped rollers. This process is done at high temperatures to minimize strain hardening of the material. However, it is relatively common for some microscopic cracks to develop at the surface of the material.

Such surface cracks are particularly critical because it effectively reduces the cross-sectional area and transverse dimension of the structural member or plate. When tension is present at the surface containing the crack, the tensile forces are concentrated at the bottom of the crack. Although this is often of no concern due to safety factors in design which keep tensile forces below levels which would cause metal fatigue, or further propagation of the crack, it may be critical in other applications in which the amount of structural material must be minimized to save weight or for other reasons. In such applications, there is no alternative to inspection of the material for surface flaws. Such inspection is difficult because of the typically small size of such flaws and the potentially large area which must be inspected.

One inspection technique, however, which is effective and sensitive for such flaw detection is referred to as magnetic particle inspection. In this technique a strong magnetic field is made to propagate through the material in a direction generally parallel to the surface to be inspected. If the field is sufficiently strong and the material brought close to magnetic saturation, any crack oriented generally perpendicular to both the surface and the magnetic field causes a strong leakage field at the surface of the material at the location of the crack (e.g. discontinuity). This leakage field can attract fine iron particles and flaws may thus be easily detected upon visual inspection. The field within the material is generally established by passing a large AC electromagnet yoke across the material surface and thus a relatively large area of material surface can be rapidly inspected.

However, the strength of the magnetic field in the material is fairly critical to the success of this inspection method. If the flux density within the material is not sufficiently great (e.g. close to saturation), the leakage field will not be caused and the flaw will not be detected. Therefore, certain standards, such as a field sufficient to lift a plate of a particular weight have been used to determine the magnetic field strength necessary for a successful test procedure. Unfortunately, this is an indirect method of testing field strength and cannot be monitored during the course of surface inspection. Since electromagnets are generally used in this test, it is common to calibrate the current used to generate the magnetic field in accordance with the standard and then monitor the current applied to the yoke of the electromagnet. This, however, is also an indirect indicator of magnetic field strength and reliable surface inspection then requires such recalibration to be frequently performed, slowing and complicating the inspection process. Even this procedure does not provide a direct indication of magnetic field strength or provide for continuous monitoring of the field strength during the inspection process.

Further, the magnetic field strength within a body of material may be greatly affected by the geometry through which the magnetic field is applied to the material. Consider for example that the surface roughness of a structural shape or plate will often be greater than the surface flaws to be detected. Thus the surface roughness presents two partial gaps in the magnetic circuit when the electromagnet yoke is applied to the surface. Therefore, the magnetic field may be diminished within the material to be inspected due to the reluctance of the partial gaps in the magnetic circuit. Thus, even frequent calibration in accordance with a standard does not guarantee that an inspection is reliable or that a sufficiently great magnetic field will be generated within the material to cause leakage fields at surface flaws.

SUMMARY OF THE INVENTION

It is therefore an object of the present invention to provide a method and apparatus for directly measuring the field strength of an electromagnet.

It is another object of the invention to provide a method and apparatus for continuously monitoring the field strength of an electromagnet.

It is a further object of the invention to provide a testing method and apparatus capable of determining a threshold strength of a magnetic field within a body of material on a continuous basis.

In order to accomplish these and other objects of the invention, a magnetic particle surface flaw inspection system is provided including an electromagnet and a magnetic field strength indicator for continuously monitoring magnetic flux in a pole piece of said electromagnet.

In accordance with another aspect of the invention, a magnetic field strength indicator for monitoring a threshold of magnetic field strength of an electromagnet is provided comprising a coupling coil arranged to be positioned around a portion of a pole piece of said electromagnet, a calibration means for adjustably altering the magnitude of a voltage induced in the coupling coil by magnetic flux, a peak rectifier circuit including a time constant circuit, and means responsive to an output of the peak rectifier circuit for providing an indication at a threshold determined by the calibration means.

In accordance with a further aspect of the invention, a method of continuously monitoring strength of a magnetic field produced by an electromagnet is provided including the steps of forming a magnetic circuit including a pole piece of the electromagnet and another element of ferromagnetic material, establishing a predetermined magnetic flux in the magnetic circuit, calibrating an indicator at a threshold level corresponding to the predetermined magnetic flux, and monitoring magnetic flux in said pole piece of said electromagnet at said threshold level.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
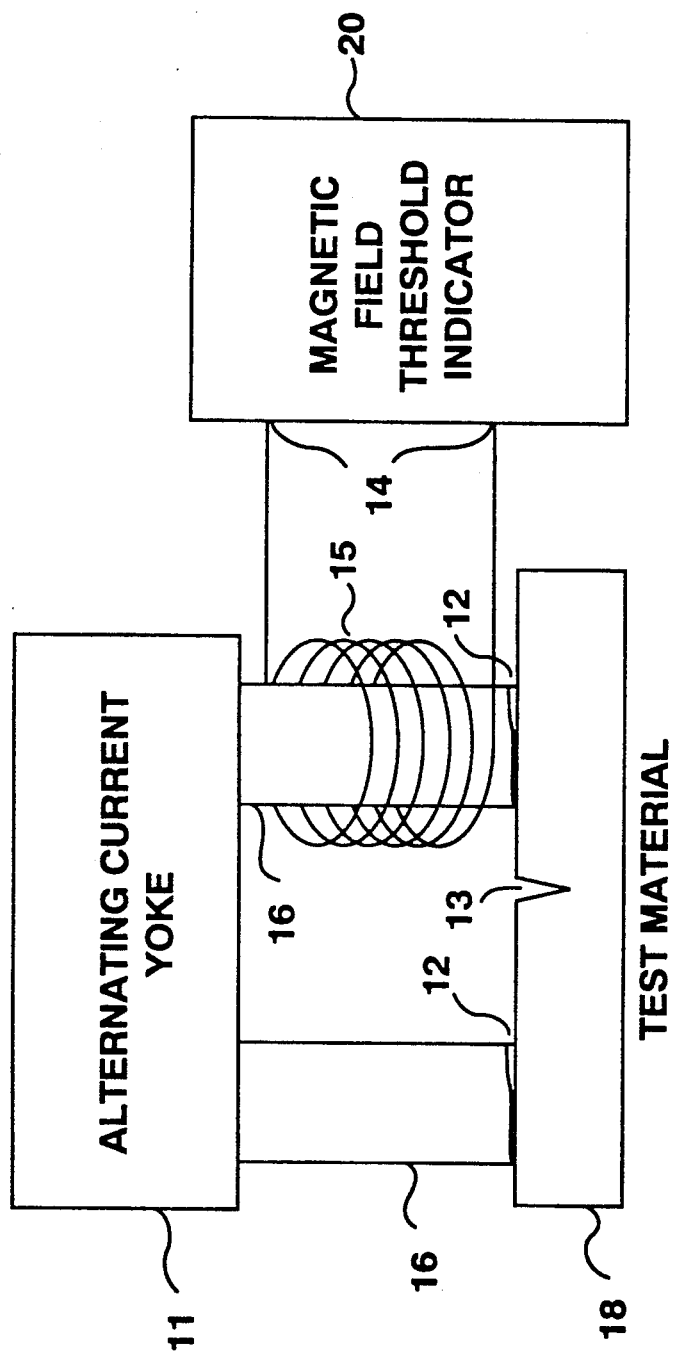
FIG. 1 is a schematic illustration of the application of the invention to magnetic particle inspection for surface flaws in a ferromagnetic material.

Referring now to the drawings, and more particularly to FIG. 1, there is schematically shown an application of the magnetic field threshold indicator in accordance with the present invention to an electromagnet in the course of magnetic particle testing. Alternating current yoke 11 includes a source of electrical current and a coil applied to a magnetic pole piece having legs 16. The ends of the legs are then placed against the surface to be inspected and the magnetic field due to the current in the alternating current yoke is propagated through a magnetic circuit including the pole piece legs 16 and the test material 18. A surface flaw such as a crack 13 causes a leakage field which can attract finely ground magnetic particles in sufficient quantity to be visually detected.

For a given current in the A.C. yoke 11, the actual strength of the magnetic field will depend on the reluctance of the magnetic circuit (e.g. the permeability and length of the materials in the circuit and the like) which potentially includes partial gaps at the interface of the legs 16 and the material 18 to be inspected. These partial gaps may be large in comparison with the flaw 13 and may cause significant variation in the field strength within the material to be tested. Of course, the permeability of the legs 16 of the electromagnet is high and the magnetic field will be substantially fully contained within the legs of the electromagnet regardless of leakage fields which may occur at- partial gaps 12 and flaws 13.

Therefore, in accordance with the invention, the field strength is directly sensed by a coil 15 encircling one leg of the electromagnet. The magnetic field thus induces a voltage in coil 15 which is communicated to the magnetic field threshold indicator 20 through coil terminals 14. In use, any fluctuation in the magnetic field strength crossing a predetermined threshold resulting from any cause can thus be detected and the reliability of the test assured. For example, if the operator of the test apparatus improperly applied the electromagnet to the surface (e.g. allowing particulate contaminants to accumulate on an end of a magnet leg 16 and causing a gap at 12) the strength of the magnetic flux in the magnetic circuit would be reduced. If the apparatus of the invention were calibrated where such a gap was not present, the reduction in flux due to the gap would cause an indication of the reduction of magnetic field strength below a threshold assuring reliability of the test. Therefore the magnetic field threshold indicator in accordance with the invention is capable of monitoring some facets of the inspection procedure, as well.

Figure 2:
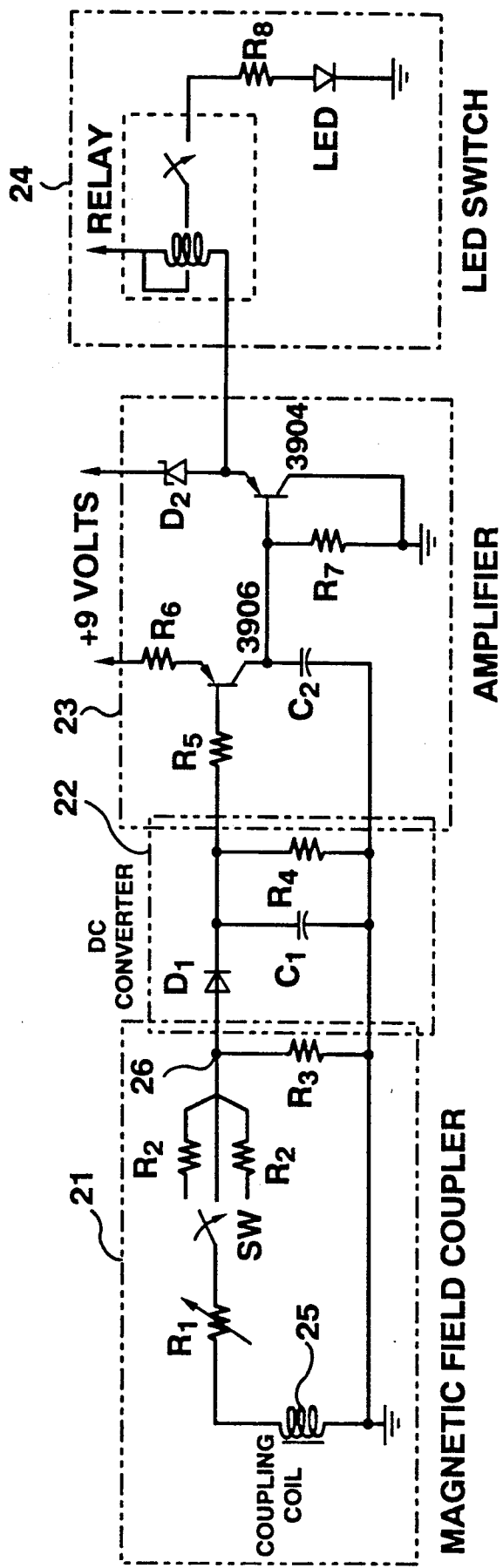
FIG. 2 is a schematic circuit diagram of the preferred embodiment of the invention.

A preferred form of the circuit of the magnetic field threshold indicator 20 is shown in FIG. 2. Since the magnetic flux is not quantitatively measured but only variation exceeding a particular threshold monitored, the circuit may be very simple and fabricated in a manner which is rugged and reliable. The circuit includes four basic stages: a magnetic field coupler 21, a D.C. converter 22, an amplifier 23 and LED switch 24.

The magnetic field coupler 21 preferably includes a coupling coil and an adjustable voltage divider for calibration of the indicator. The coupling coil 25 is preferably formed as a 600 turn inductor wrapped on a non-conductive thermoplastic thimble of a diameter which can be placed on a leg 16 of the electromagnet. The voltage divider includes an adjustable trimming resistor $R_1$, in series with a fixed resistor R3. To provide a range of voltage division, a rotary switch SW which can selectively add one of any number of further fixed resistors R2, R2', etc. in series with R3 and $R_1$. The output of the voltage divider is thus taken at node 26 and a wide range of voltages induced in coil 25 by a wide range of magnetic flux densities can be accommodated.

The D.C. converter stage 22 is simply a peak rectifier having a time constant circuit and can be of any known form. In the preferred form of the circuit, the rectifier is a single diode (D1) half-wave rectifier and the time constant is provided as a simple RC circuit including a parallel connection of R4 and C1. The time constant should be many times greater than the period of the energizing current but should also allow detection of mechanical movements of the electromagnet which cause reduction of magnetic field strength in the tested material. Since the threshold can be closely calibrated, a time constant of several seconds has been found to be adequate.

Amplifier stage 23 is a simple two transistor amplifier but could also be made in other forms. The function of the amplifier could be described as "inverting" since a high input voltage holds the output transistor in the "OFF" state. The amplifier shown can be preferably powered by a small and light weight 9 volt battery to allow the indicator to be self-contained and conveniently positioned for observation by the inspection system operator. Zener diode D2 is arranged at the amplifier output to parallel the indicator relay 27 and to conduct at 5.1 volts to increase response speed and avoid saturation of a relay used to control the LED indicator of the LED switch stage 24. It is to be understood that any other type of visual, audible tactile, etc. indicator could be used as an alarm annunciator, particularly with the switching function provided by the relay. However, a light-emitting diode indicator is preferred for reliability, light weight, small size, low voltage requirements and battery drain and high intensity visual output.

In use, the magnetic field indicator arrangement in accordance with the invention can be calibrated while lifting a weight in accordance with the present standard to the extent of lifting a predetermined weight with the electromagnet. At a given magnetic field strength or flux density, resistor $R_1$ is adjusted to the point where the LED indicator transitions from the "ON" state to the "OFF" state. After the indicator has been thus calibrated, the field strength of the electromagnet can be continuously monitored by the indicator in accordance with the invention. as long as the indicator remains in the "OFF" state, the operator is assured of a sufficient field strength for reliable inspection by the magnetic particle technique. Of course, either the function of the relay or the amplifier could be inverted to provide a positive indication of sufficient magnetic field strength. However, the reliability of the indicator is such that operation as an alarm when the magnetic field strength drops below a threshold has been found to be most convenient for the operator and is consistent with minimum battery drain.

While the invention has been described in terms of a single preferred embodiment, those skilled in the art will recognize that the invention can be practiced with modification within the spirit and scope of the appended claims. In particular, while the invention has been described in the context of magnetic particle surface flaw inspection, it is equally applicable to any other environment where a threshold of magnetic field strength or flux density is monitored. Further, a plurality of indicator circuits could be provided for redundancy at the same threshold or calibrated at different thresholds to provide a coarse measurement of field strength. Also, a combination of inverting and non-inverting functions of the amplifiers and relays in such plural circuits, possibly including a logical combination of the outputs with simple logic gates could be used to monitor a range of magnetic field strengths and flux densities.

Having thus described my invention, what I claim as new and desire to secure by Letters Patent is as follows:

1. A magnetic field strength indicator for monitoring a threshold of magnetic field strength of an electromagnet comprising:
   a coupling coil arranged to be positioned around a portion of a pole piece of said electromagnet,
   a calibration means for adjustably altering the magnitude of a voltage included in said coupling coil by magnetic flux passing through said pole piece said calibration means comprising a voltage divider connected across said coil, said voltage divider including a switch in series with the parallel combination of at least two resistors in series with a third resistor,
   a peak rectifier circuit including a time constant circuit connected across said third resistor,
   an amplifier for receiving the output of said peak rectifier circuit;
   means responsive to an output of said amplifier for providing an indication at a threshold determined by said calibration means,
   said means responsive including a relay and a light emitting diode and relay activating said diode wherever the said threshold is exceeded.

* * * * *